United States Patent [19]
Weier

[11] Patent Number: 5,843,176
[45] Date of Patent: Dec. 1, 1998

[54] SELF-EXPANDING ENDOPROSTHESIS

[75] Inventor: Steven D. Weier, Miramar, Fla.

[73] Assignee: Cordis Corporation, Miami Lakes, Fla.

[21] Appl. No.: 934,707

[22] Filed: Sep. 22, 1997

Related U.S. Application Data

[62] Division of Ser. No. 733,129, Oct. 17, 1996, abandoned.

[51] Int. Cl.$^6$ ....................................................... A61F 2/06
[52] U.S. Cl. .................................. 623/1; 606/195; 600/36
[58] Field of Search .................................. 623/1, 11, 12; 606/194, 195, 198; 600/36

[56]  References Cited

U.S. PATENT DOCUMENTS

| | | |
|---|---|---|
| 4,425,908 | 1/1984 | Simon . |
| 4,553,545 | 11/1985 | Maass et al. . |
| 4,580,568 | 4/1986 | Gianturco . |
| 4,655,771 | 4/1987 | Wallsten . |
| 4,830,003 | 5/1989 | Wolff et al. . |
| 5,275,622 | 1/1994 | Lazarus et al. .............................. 623/1 |

FOREIGN PATENT DOCUMENTS

| | | |
|---|---|---|
| 423916 | 4/1991 | European Pat. Off. . |
| WO9313825 | 7/1993 | WIPO . |

OTHER PUBLICATIONS

Duprat et al, "Self–Expanding Metallic Stents for Small Vessels: An Experimental Evolution", Radiology, vol. 162, pp. 469–472, Feb. 1987.

*Primary Examiner*—Debra S. Brittingham
*Attorney, Agent, or Firm*—Lockwood, Alex, Fitz-Gibbon & Cummings

[57]   ABSTRACT

A stent or other endoprosthesis is provided from a single strand of biocompatible and resilient material into which spring coils are formed by winding the strand through in excess of 360°. The thus-formed coil springs are positioned along outside edges of the endoprosthesis, with legs joining the coil springs in order to form a generally zig-zag structure. When the endoprosthesis is compressed for endoluminal delivery, the coil springs allow for large angular deflection between adjoining legs while avoiding plastic deformation of the coil or of the legs.

16 Claims, 1 Drawing Sheet

SELF-EXPANDING ENDOPROSTHESIS

This application is a division of application Ser. No. 08/733,129, filed Oct. 17, 1996, now abandoned.

BACKGROUND AND DESCRIPTION OF THE INVENTION

This invention generally relates to endoprostheses, also known as stents, which are of the self-expanding type. More particularly, the invention relates to self-expanding stents or other endoprostheses which are deployed in a compressed condition under radial tension and which are implanted by removing a restraining member so as to permit the radial tension to expand the stent or the like within a body vessel so as to be supportive of the vessel at that location. The endoprosthesis is made of a continuous strand shaped as a generally cylindrical member and having a plurality of coil spring portions wound from the strand so as to impart the above-mentioned radial tension.

So-called stenting has come to be accepted as a viable interventional medical procedure in many specific situations where vessels require support on a long-term basis. Other endoluminal devices or endoprostheses such as vena-cava filters have also been developed or proposed. Typically, catheters or catheter-like devices are used to carry out an endoluminal implantation of these stents or other endoprostheses. The catheter or the like is used to transport the stent or the like into and through a body vessel such as a blood vessel until the stent or the like is positioned at a target location. Once at the target location, the stent or the like is deployed in order to provide the desired internal support of the vessel or other treatment at the deployment location.

Typically, the deployment location is the site of disease, injury, or other imperfection in the body vessel. Typical disease patterns involve stenosis development causing a blockage or partial blockage at the target site. For example, angioplasty procedures are well-known for addressing stenoses and opening up body vessels that have a constriction due to plaque buildup or the like. With such procedures, radially outwardly directed forces are applied to the lumen of the stenosis, such as by the inflation of an angioplasty balloon. Often, it is deemed to be desirable to leave a device in place at the site of the thus-expanded lumen of the stenosis. Such a device is believed to provide support for the vessel wall which might be weakened at that location, while also providing a scaffolding type of structure about which endothelium development, for example, can occur in order to repair the diseased, injured or damaged area.

Some such endoprostheses are deployed with an angioplasty catheter, either during the angioplasty procedure or after the angioplasty procedure has opened up the stenosis. These are so-called balloon-deployed stents or endoprostheses. The stents themselves are capable of being moved from a smaller circumference to a larger circumference by the action a device such as the balloon of an angioplasty catheter. These require a device such as a balloon catheter in order to achieve the radial expansion needed for stent deployment within the body vessel. Other types of stents are of the self-expanding variety. With these, a device, typically a simple cylindrical sheath over the stent, holds the stent or other endoprosthesis at a reduced diameter during passage through the body vessel. Once the treatment site is reached, the sheath or other device is removed from around the stent, and the stent self-expands in place.

The present invention is directed to stents or other endoprostheses which are of this self-expanding variety. It is important in these types of devices that the expansion qualities be predictable so that the outwardly radially directed tension present in the compressed stent or the like will not vary depending upon the amount that the stent or the like is compressed either before or during deployment. It is also important that this tension not be compromised if the stent or the like is compressed and self-expanded multiple times.

One difficulty with certain prior art self-expanding stents is that their outwardly directed tension can dissipate due to plastic deformation of small areas of the stent which must bend in order be compressed for deployment and which then must unbend in order to achieve the needed stent self-expansion. Inconsistencies in outwardly directed radial tension due to variations in the extent of any such plastic deformation can lead to inconsistencies in deployment, potentially leading to ineffective stent implantation. For example, if plastic deformation has reduced the otherwise expected amount of outwardly directed radial tension, the stent might not open to an adequate extent to ensure that the stent will remain in place after deployment for a desired length of time, usually for several years. In other words, the hoop strength of the deployed stent might not be adequate due to plastic deformation. Conversely, if the stent is designed to account for an expected degree of plastic deformation, but the stent, for example, is not compressed as much as anticipated by the designer, the tension in the implanted stent might be too great for the particular treatment or intervention being carried out.

Typically, these types of deficiencies are found in self-expanding stents which operate on a principal of cantilever action. In general, the material of such stents or the like flexes at a focal point. These localized forces can lead to the undesirable plastic deformation of the material at such focal points. Focal points of this type are found in joints which operate as living hinges or which include solder or weld sites at or adjacent to flexible focal points. These types of structures set up a condition where the material of the stent or the like simply bends in a generally cantilevered manner as described.

SUMMARY OF THE INVENTION

In accordance with the present invention, it has been determined that important advantages can be obtained when a stent or other endoprosthesis is provided with self-expanding joints which are wound coil springs which allow for large angular deflection between adjoining legs of the device. The coils operate in the nature of coil springs which allow the stent or the like to open and close numerous times without developing plastic deformation caused by flexing at a focal point. Instead, the coil spring coils more tightly but only sufficiently to accommodate compression of the stent or the like. Likewise, the coil spring then uncoils as needed for deployment. The spring coil and its adjacent legs are part of a continuous strand of the stent material, the stent material having been wound through in excess of 360° at the locations of the coil springs in order to form the coils and the legs of the stent or other endoprosthesis.

It is accordingly a general object of the present invention to provide an improved stent or other endoprosthesis which is of the self-expanding type.

Another object of the present invention is to provide an improved self-expanding stent or the like which avoids plastic deformation at bend locations which impart self-expansion properties to the device.

Another object of this invention is to provide an improved self-expanding endoprosthesis having a plurality of legs, the respective lengths of which define the overall shape of the endoprosthesis as being either right cylindrical or spirally wrapped cylindrical.

Another object of the present invention is to provide an improved self-expanding endoprosthesis which has a high expansion ratio and a high hoop strength and which will spring back to its as-manufactured shape even if flattened by an excessive external load.

Another object of the present invention is to provide an improved method for forming a self-expanding endoprosthesis which includes winding a strand into a coil spring which is then flanked by a pair of strand legs.

Another object of this invention is to provide an improved endoprosthesis and method which provides a substantially consistent expansion ratio and hoop strength which does not vary significantly with the degree of reasonable compression and/or expansion.

These and other objects, features and advantages of the present invention will be apparent from and clearly understood through a consideration of the following detailed description.

BRIEF DESCRIPTION OF THE DRAWINGS

In the course of this description, reference will be made to the attached drawings, wherein.

DETAILED DESCRIPTION OF THE INVENTION

Figure 1:
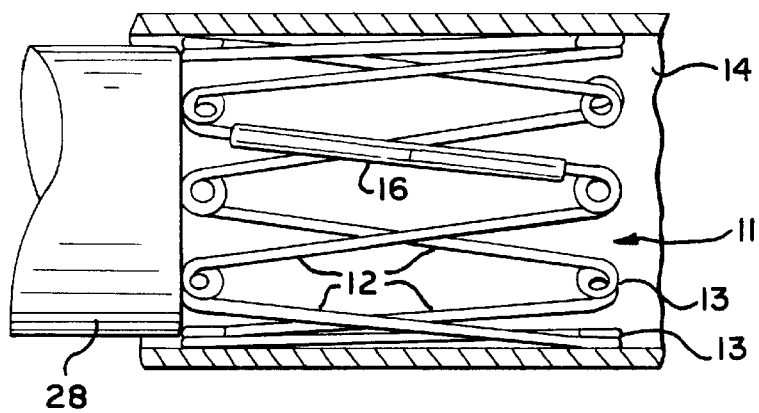
FIG. 1 is a side elevational view of a preferred stent according to the invention, shown in an unexpanded condition within a tube shown in cross-section.

A stent in accordance with the present invention is generally designated as 11 in FIG. 1. Stent 11 includes a plurality of legs 12. Each pair of legs has a coil 13 positioned therebetween such that a pair of legs flanks each coil. In FIG. 1, the stent 11 is shown in a compressed state, this state of compression being maintained by a suitable device such as illustrated delivery tube 14 which prevents the stent from expanding beyond the condition shown in FIG. 1.

Figure 2:
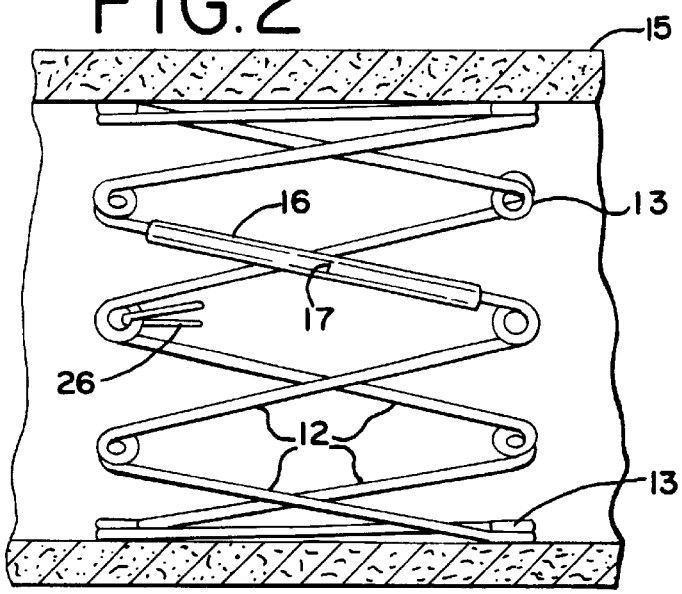
FIG. 2 is an elevational view of the stent illustrated in FIG. 1, shown expanded within a body vessel, illustrated in cross-section.

With reference to FIG. 2, the stent of FIG. 1 is shown deployed within a body vessel 15, such as a blood vessel or the like. In this deployed condition, the stent has self-expanded so as to engage the body vessel and remain so engaged even in the face of blood flow, for example, through the body vessel. Thus, in the deployed condition, the stent is still biased or under tension in an outward radial direction. In other words, the stent as shown in FIG. 2 has not reached the limit of its self-expansion potential. It exhibits adequate hoop strength so as to maintain the stent in its deployed location by exerting an adequate, but not excessive, force on the inside wall of the body vessel.

In the structure shown in FIG. 1 and in FIG. 2, each leg 12 is of virtually the same length. The result is a right cylindrical stent configuration. The formed strand which makes up this stent configuration forms the cylinder by wrapping full circle through 360° as shown. Respective ends of the strand making up the stent are secured together by suitable means such as welding, soldering, adhesives, or by the use of a sleeve 16 or the like. Illustrated sleeve 16 takes the form of a hypotube, such as one having a wall thickness of about 0.002 inch (about 0.05 mm). Each end 17 of the strand is securely positioned within the sleeve 16. Preferably, the sleeve or the like securely holds the strand ends with respect to each other so as to prevent torquing or twisting of the end portions of the strand with respect to each other.

Figure 3:
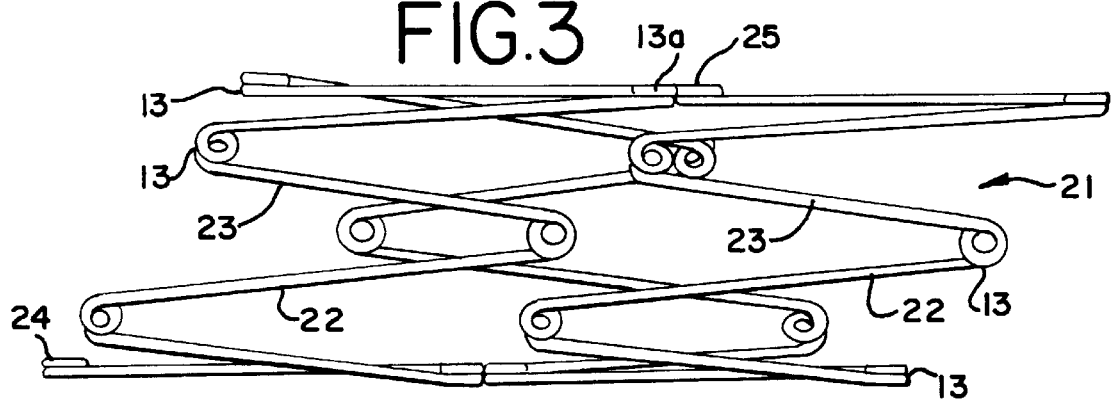
FIG. 3 is an elevational view of an alternative embodiment of a stent according to the invention.

An alternative embodiment is the stent which is generally designated as 21 in FIG. 3. Stent 21 includes coils 13 as in the first embodiment. The legs 22, 23 of this second embodiment have differing lengths. These differing lengths generally alternate between a longer length and a shorter length. The result as illustrated is to have the stent take on a generally helical configuration in forming an overall cylindrical device. This is done without substantially modifying the parallel relationship between respective alternating legs, as is evident in FIG. 3. This helical winding arrangement is such as to also allow for the legs to generally squarely engage a cylinder positioned around them, such as a delivery tube or a body vessel by being generally parallel to the axis of such a cylinder.

In the embodiment illustrated in FIG. 3, the strand pattern wraps through about 540°. That is, the configured strand pattern is wrapped for one full circumference followed by one half of that same circumference. Thus, the stent 21 begins at an end portion 24 and continues through to an end portion 25. While both end portions are shown to be coiled, other end treatments could be suitable. These could be straight ends, bent ends, or ends attached to adjacent portions of the stent. For example, if second end 25 is welded or otherwise secured to coil 13A adjacent to it, the stent will be more likely to maintain the 540° wrap which is illustrated during compression and deployment. Even without such an attachment, this degree of wrap will not vary significantly between the compressed state and the deployed state. This is because the coils will tend to spring open in a very uniform manner, with the result that the extent of springing expansion will be generally uniform throughout the stent.

It will be appreciated that other stent wrapping lengths are possible depending upon the particular need. For example, if the stent were wrapped for two full circumferences, its longitudinal length would be larger than that shown in FIG. 3.

With further reference to possible lengths of stents 11, 21, such stents can be lengthened by securing them together or by deploying them in an end-to-end fashion. When attachment is desired, this can be achieved by attachment means such as sutures or by one or more radiopaque marking bands 26 (FIG. 2) which can be used to join adjacent stents together (not shown). Such marking bands 26 can also be used only to aid in radioscopic viewing without performing a tying function. Alternatively, adjacent stents can be positioned so as to overlap with each other such that the legs of one stent engage respective legs of another stent.

It will further be appreciated that the length and the diameter of each stent also can be tailored to address specific needs. This can be done by changing the length of the legs and the number of coils. Varying the number of coils will, with all other things being equal, vary the hoop strength and expansion ratio of each particular stent. Varying the size of the coils is also possible, whether the variation is in the circumference of the coils or the number of wraps used to form the coils.

A greater appreciation for the structural features of the stents or other endoprostheses in accordance with the present invention can be gained by considering the method by which these devices are constructed. In the preferred method, a single strand of suitable material is formed into the stent. A fence, ribbon or configured strand pattern is first formed. Each coil is formed by turning the strand on itself in a circumferential manner, typically by winding a length of the stand over a mandrel or wire so that the coil extends for greater than one full circumference. Spaces between coils define the legs, with alternating coils being wound in opposite directions, one clockwise and the next one counterclockwise, and so forth.

In the preferred arrangement, the extent of coiling beyond a full circle winding can range between about 130° and about 180°. A preferred range is between about 150° and about 170° in excess of one or more full circle windings. For example, if less than two full circle coils are desired (as illustrated in the drawings), this coil winding range will be between about 490° and about 540°, preferably between about 510° and about 530°. Adding another full circle wind would mean coils of between about 850° and about 900°, preferably between about 870° and about 890°.

This winding degree is that of the coil when it is fully expanded. It will be appreciated that, when deployed within a body vessel, a predetermined amount of tension should remain within the coils; that is, they will remain compressed somewhat, and when the coils are made, they will be wound to an untensioned winding degree. In a typical application, for example, a coil which is wound to 510° could be compressed to 530° or more when within the delivery tube 14 such as illustrated in FIG. 1 and will expand to about 520° when deployed such as illustrated in FIG. 2.

The fence, ribbon or configured strand pattern thus formed is then wrapped in a circumferential manner and the ends secured when desired. For example, in the first embodiment, the sleeve is used to assemble the ends 17 of the strand.

The strand material should exhibit sufficient resiliency so as to be suitable for forming a coil spring. In addition, the material should be biocompatible or securely coated in a biocompatible manner. Exemplary materials include stainless steel, titanium, Nitinol alloys of nickel and titanium, as well as possible polymers which exhibit the required degree of resiliency.

It will be appreciated that, with the spring coil arrangement, the coil itself provides most of the springiness or tension to the stent. Rather than having flexing occur at a focal point, the entire spring material moves or rotates in the well-known manner of a coiled spring such as that of a safety pin so that the tension is relatively evenly distributed throughout the extent of the coil spring. The coils allow for a large angular deflection between adjoining legs without plastic deformation of the material of the strand, coil or legs. With this coil spring structure, the stent will spring back to shape even if it were to be totally collapsed by an extraordinary external load.

With reference to the deployment procedure for a self-expanding stent of the type discussed herein, a typical stent will have an overall length of on the order of 2 cm. This length can be greater or longer as desired and as needed for particular applications. For example, lengths may range between about 1 cm and about 4 cm. The entire stent or other endoprosthesis is compressed and positioned within the inside of the delivery tube 14. This delivery tube can take the form of a guiding catheter, for example. This delivery tube or guiding catheter is inserted into and fed through appropriate body passageways such as blood vessels in accordance with well-known medical procedures, such as those followed for angioplasty treatments. Once the open distal tip end of the delivery tube or guiding catheter is positioned at the body location at which the stent is to be deployed, the compressed stent is moved out of the open distal end of the delivery tube or guiding catheter. A typical means for accomplishing this is to use a push rod 28 (FIG. 1) which can take the form of a simple wire that readily slides through the delivery tube or guiding catheter and which has an outer diameter adequate to fully engage the full circumference of the stent or the like. When thus engaged, the push tool 28 will slide the compressed stent out of the distal hole, allowing it to expand in place within the body vessel as generally shown in FIG. 2.

Should it become necessary to retrieve one of these stents after deployment, this is possible. For example, a guiding catheter can be positioned with its distal end opening closely proximal to the deployed stent or other endoprosthesis. A biopsy forceps device can then be fed through the guiding catheter and used to snare the deployed stent or the like and pull it into the guiding catheter. Thereafter, removal of the guiding catheter will safely remove the stent or the like.

It will be understood that the embodiments of the present invention which have been described are illustrative of some of the applications of the principles of the present invention. Numerous modifications may be made by those skilled in the art without departing from the true spirit and scope of the invention.

I claim:

1. A self-expanding endoprosthesis for insertion into and implantation within a living body vessel, comprising:

a continuous strand of biocompatible and resilient material, said strand formed into a generally cylindrical endoprosthesis which is self-expanding from a compressed orientation for delivery into a living body vessel so as to assume an expanded orientation, the expanded orientation being larger in circumferential degree than said compressed orientation and being an orientation at which the endoprosthesis is deployed into supporting engagement with an inside wall of the living body vessel;

said continuous strand includes a plurality of alternating leg portions and coil portions, each said coil portion being a coil spring wound from said continuous strand to form a coil spring winding through in excess of 360°;

different ones of said leg portions have different lengths, one length defining a longer length leg portion and another length defining a shorter length leg portion, wherein one said shorter length leg portion and one said longer length leg portion are Joined together at one of said coil portions; and said coil portions are positioned so as to define at least one generally helical path of coil portions along the endoprosthesis.

2. The self-expanding endoprosthesis in accordance with claim 1, wherein at least some of said coil springs have an as-wound orientation which is smaller in circumferential degree than said expanded orientation.

3. The self-expanding endoprosthesis in accordance with claim 2, wherein said coil spring is substantially untensioned when at the as-wound orientation.

4. The self-expanding endoprosthesis in accordance with claim 1, wherein said leg portions and coil portions define a configured strand pattern which is wound through at least 360° to define the generally cylindrical endoprosthesis.

5. The self-expanding endoprosthesis in accordance with claim 1, wherein said coil spring varies in coil tension between said compressed and expanded orientations, said coil spring having a greater tension in the compressed orientation than in the expanded orientation.

6. The self-expanding endoprosthesis in accordance with claim 1, wherein said coil spring provides a site of generally rotational springing flexing for substantially eliminating plastic deformation of the coil spring and of each leg adjacent thereto in response to radially directed compression of the endoprosthesis.

7. The self-expanding endoprosthesis in accordance with claim 1, wherein said coil spring winding is between about 130° and about 180° in excess of at least one full circle winding.

8. The self-expanding endoprosthesis in accordance with claim 7, wherein said coil spring winding is between about 510° and about 530°.

9. The self-expanding endoprosthesis in accordance with claim 1, wherein said continuous strand is a steel wire.

10. The self-expanding endoprosthesis in accordance with claim 1, wherein said coil portions are wound in opposite directions along said strand and clockwise-wound coil portions alternate with counterclockwise wound coil portions.

11. The self-expanding endoprosthesis in accordance with claim 1, further including a radiopaque marker secured to said endoprosthesis.

12. The self-expanding endoprosthesis in accordance with claim 1, wherein said strand has an initial end and a terminal end, and said ends are secured together.

13. A process for manufacturing a self-expanding endoprosthesis, comprising the steps of:

provifing a continuous strand of biocompatible and resilient material;

winding said strand through in excess of 360° so as to form a first coil spring portion therealong;

repeating said winding step at a location spaced from said first coil spring portion in order to form a second coil spring portion which is spaced from said first coil spring portion by a predetermined distance and thus accomplishing a step of defining a leg portion of the endoprosthesis therebetween;

said defining step provides legs of at least two different lengths in an alternating manner, said wrapping step proceeds through greater than 360°, and after said wrapping step, said configured strand pattern has a generally helical appearance;

continuing said winding and defining steps until a desired number of coil spring portions are formed, in order to thereby form a configured strand pattern having the leg portions alternating with the coil spring portions; and wrapping said configured strand pattern through a generally cylindrical plane in order to form a generally cylindrical endoprosthesis.

14. The method according to claim 13, wherein said wrapping step proceeds through at least 360°.

15. The method according to claim 13, wherein said winding step for forming the coil spring winds the strand through between about 130° and about 180° in excess of one or more full circle windings.

16. The method in accordance with claim 15, wherein said winding step winds the strand through between about 510° and about 530°.

* * * * *

UNITED STATES PATENT AND TRADEMARK OFFICE
CERTIFICATE OF CORRECTION

PATENT NO. : 5,843,176
DATED : December 1, 1998
INVENTOR(S) : Steven D. Weier

It is certified that error appears in the above-identified patent and that said Letters Patent is hereby corrected as shown below:

Col. 2, line 12, "order be" should read --order to be--.
Col. 5, line 5, "stand" should read --strand--.
Col. 6, line 49, delete "Joined" and insert --joined--.

Signed and Sealed this

Fourth Day of July, 2000

Attest:

Q. TODD DICKINSON

Attesting Officer        Director of Patents and Trademarks